United States Patent
Meyer-Lückel et al.

(10) Patent No.: US 7,485,673 B2
(45) Date of Patent: Feb. 3, 2009

(54) METHOD OF INFILTRATING ENAMEL LESIONS

(75) Inventors: Hendrik Meyer-Lückel, Berlin (DE); Sebastian Paris, Neuruppin (DE); Andrij M. Kielbassa, Berlin (DE)

(73) Assignee: Charite-Universitatsmedizin Berline, Berlin (DE)

( * ) Notice: Subject to any disclaimer, the term of this patent is extended or adjusted under 35 U.S.C. 154(b) by 382 days.

(21) Appl. No.: 11/040,442

(22) Filed: Jan. 21, 2005

(65) Prior Publication Data

US 2006/0167129 A1    Jul. 27, 2006

(51) Int. Cl.
*A61K 6/00* (2006.01)
*A61K 6/083* (2006.01)

(52) U.S. Cl. .................. 523/115; 523/116; 523/118

(58) Field of Classification Search .............. 523/115, 523/116, 118; 424/78.08; 423/481
See application file for complete search history.

(56) References Cited

U.S. PATENT DOCUMENTS

| | | | |
|---|---|---|---|
| 6,326,417 B1 * | 12/2001 | Jia | 523/116 |
| 6,482,871 B1 * | 11/2002 | Aasen et al. | 523/116 |
| 6,753,001 B2 * | 6/2004 | Jia et al. | 424/401 |
| 2003/0157034 A1 * | 8/2003 | Jia et al. | 424/49 |
| 2003/0175218 A1 * | 9/2003 | Kanca, III | 424/49 |
| 2006/0167129 A1 | 7/2006 | Meyer-Luckel et al. | |

FOREIGN PATENT DOCUMENTS

FR    2 542 198 A1    9/1984

OTHER PUBLICATIONS

Davila, J.M. et al. "Adhesive penetration in human artificial and natural white spots" *J Dent Res*, 1975, 54:999-1008.
De Araujo, F.B. et al. "Diagnosis of approximal caries: Radiographic versus clinical examination using tooth separation" *Am J Dent*, 1992, 5:245-248.
Ekstrand, K.R. and Martignon, S. "Managing approximal carious lesions: A new non-operative approach" *Caries Res*, 2004, 38:361, abstract No. 12.
García-Godoy, F. et al. "Caries progression of white spot lesions sealed with an unfilled resin" *J Clin Pediatr Dent*, 1997, 21:141-143.
Goepferd, S.J. and Olberding, P. "The effect of sealing white spot lesions on lesion progression in vitro" *Pediatric Dent.*, 1998, 11:14-16.
Gray, G.B. and Shellis, P. "Infiltration of resin into white spot caries-like lesions of enamel: An in vitro study" *Eur J Prosthodont Restor Dent*, 2002, 10:27-32.

(Continued)

*Primary Examiner*—Mark Eashoo
*Assistant Examiner*—Michael Pepitone
(74) *Attorney, Agent, or Firm*—Baker & Daniels LLP

(57) ABSTRACT

The present invention refers to a method of infiltrating enamel, in particular for the prevention and/or treatment of carious lesions. Said method of infiltrating enamel comprises the steps of (a) exposing an enamel area to be infiltrated to a conditioner comprising hydrochloric acid; (b) exposing the enamel area conditioned in step (a) to an infiltrant comprising at least one low viscous dental resin; and (c) curing the infiltrant. The present invention further refers to a kit for carrying out said method.

13 Claims, 3 Drawing Sheets

OTHER PUBLICATIONS

Hamid, A. and Hume, W.R. "Diffusion of resin monomers through human carious death in vitro" *Endod Dent Traumatol*, 1997, 13:1-5.

Kogon, S.L. e t al. "Can radiographic criteria be used to distinguish between cavitated and noncavitated approximal enamel caries?" *Dentomaillofac Radiol*, 1987, 16:33-36.

Larsen, M.J. and Fejerskov, O. "Surface etching and subsurface demineralization of dental enamel induced by a strong acid" *Scand. J. Dent. Res.*, 1977, 85:320-326.

Marthaler, T.M. and Germann, M. "Radiographic and visual appearance of small smooth surface caries lesions studied on extracted teeth" *Caries Res*, 1970, 4:224-242.

Majàre, I. et al. "Caries development from 11 to 22 years of age: A prospective radiographic study" *Caries Res*, 1998, 32:10-16.

Meyer-Lueckel, H. et al. "Influence of the application time on the penetration of different dental adhesives and a fissure sealant into artificial subsurface lesions in bovine enamel" *Dent Mat*, 2006, 22:22-28.

Meyer-Lueckel, H et al. "The penetration of various adhesives into initial enamel lesions in vitro" *Schweiz Monatsschr Zahnmed*, 2005, 155:134-323, summary—p. 323.

Ratledge, D.K. et al. "A clinical and microbiological study of approximal carious lesions" *Caries Res*, 2001, 35:3-7.

Robinson, C. et al. "In vitro studies of the penetration of adhesive resins into artificial caries-like lesions" *Caries Res*, 2001, 35:136-141.

Robinson, .C et al. "Arrest and control of carious lesions: A study based on preliminary experiments with resorcinol-formaldehyde resin" *J Dent Res*, 1976, 55:812-818.

Rugg-Gunn, A.J. "Approximal carious lesions—A comparison of the radiological and clinical appearances" *Br Dent J*, 1972, 133:481-484.

Schmidlin, P.R. et al. "Sealing smooth enamel surfaces with a newly devised adhesive patch: a radiochemical in vitro analysis" *Dent Mater*, 2005, 21:545-550.

Schmidlin, P.R. et al. "Penetration of a bonding agent into De- and remineralized enamel in vitro" *J Adhes Dent*, 2004, 6:111-115.

Seemann, R. et al. "Caries preventive potential of an adhesive patch for proximal sealing: A microbial-based in vitro study" *Caries Res.*, 2005, 39:321, abstract No. 101.

Spurr, A.R. "A low-viscosity epoxy resin embedding medium for electron microscopy" *J Ultrastruct Res*, 1969, 26:31-43.

Paris, S. "Sealing of initial enamel lesions with various adhesives and a fissure sealant at different penetration times in vitro" Doctoral thesis at Fachbereich Humanmedizin, Freie Universität Berlin, 2005; Table of Contents (German), Summary (English), and English translation of pp. 55-56.

* cited by examiner

METHOD OF INFILTRATING ENAMEL LESIONS

The present invention refers to a method of infiltrating enamel, in particular for the prevention and/or treatment of carious lesions. The present invention further refers to a kit for carrying out said method of infiltrating enamel, which comprises a conditioner comprising hydrochloric acid and an infiltrant comprising at least one low viscous dental resin.

FIELD OF THE INVENTION

In industrial countries, about 98% of the adult population exhibits one or more carious lesions or are already provided with fillings. Any carious lesion which eventually may lead to cavitation is initiated by demineralization of the hard tooth substance. At an early stage, referred to as "initial enamel caries", the tooth surface remains intact without visible signs of erosion but the demineralized area below the surface becomes more and more porous.

Today, the only non-operative ways to treat approximal caries are to enhance remineralization by application of fluorides and to arrest lesion progress by improvement of patient's oral hygiene. While smooth surfaces of the tooth are more susceptible for improved cleaning strategies, approximal surfaces are particularly difficult to clean. Nevertheless, remineralization in approximal lesions that have reached the dentin seems to be hardly achievable, since several clinical studies showed that from this threshold a visible cavitation of the lesion is established in most cases (Rugg-Gunn, A J. Approximal carious lesions. A comparison of the radiological and clinical appearances. *Br Dent J,* 1972, 133:481-484; De Araujo, F B et al. Diagnosis of approximal caries: radiographic versus clinical examination using tooth separation. *Am J Dent,* 1992, 5:245-248; Ratledge et al. A clinical and microbiological study of approximal carious lesions. Part 1: The relationship between cavitation, radiographic lesion depth, the site-specific gingival index and the level of infection of the dentine. *Caries Res,* 2001, 35:3-7). Moreover, in vitro studies even found many cavitations in lesions confined to enamel. A cavitated enamel lesion cannot be cleaned sufficiently by the patient and will progress (Marthaler, T M and Germann, M. Radiographic and visual appearance of small smooth surface caries lesions studied on extracted teeth. *Caries Res,* 1970, 4:224-242; Kogon, S L et al. Can radiographic criteria be used to distinguish between cavitated and noncavitated approximal enamel caries? *Dentomaillofac Radiol,* 1987, 16:33-36). Therefore, if a cavitation occurs even at such an early stage of the caries process, a remineralization seems very unlikely under clinical conditions. This could explain clinical findings, that fluoridation and improved oral hygiene can only slow down the progression of approximal caries but are not capable of reversing it (Mejare, I et al. Caries development from 11 to 22 years of age: A prospective radiographic study. Prevalence and distribution. *Caries Res,* 1998, 32:10-16).

Once a cavitation has developed, invasive methods of treatment are generally indicated. However, drilling out carious tooth material is always accompanied by the removal of non-carious, i.e. sound, hard tooth substance. In approximal carious lesions which are difficult to reach, the ratio of carious and intact substance being removed is particularly unfavorable. Moreover, the connection between an inserted filling and the endogenous tooth material is susceptible for carious lesions itself, and renewal of fillings due to the ageing process leads to further removal of sound tooth material. Therefore, methods of treating caries at an early stage, and in particular approximal initial carious lesions, are highly desirable in order to prevent later requirement for invasive procedures.

One apparent indication of initial enamel caries are white spot lesions. Such a lesion is characterized by a loss of mineral in the bulk of enamel, whereas the surface of the lesion remains relatively intact (so-called "pseudo-intact surface layer"). A promising approach of non-operative dentistry might be the sealing of enamel lesions with low viscous light curing resins such as dental adhesives and fissure sealants. The tiny pores within the lesion body act as diffusion pathways for acids and minerals and, therefore, enable the dissolution of enamel at the advancing front of the lesion. The aim of the proposed regimen is not only to seal the surface but to infiltrate these pores, thereby withdrawing the lesion body from further attack. Moreover, after curing the resin material, a mechanical support of the fragile enamel framework in the lesion will be achieved.

The idea to arrest caries by sealing with low viscous resins has been followed in a few in vitro experiments since the seventies of the last century (Robinson, C et al. Arrest and control of carious lesions: A study based on preliminary experiments with resorcinol-formaldehyde resin. *J Dent Res,* 1976, 55:812-818; Davila, J M et al. Adhesive penetration in human artificial and natural white spots. *J Dent Res,* 1975, 54:999-1008; Gray, G B and Shellis, P. Infiltration of resin into white spot caries-like lesions of enamel: An in vitro study. *Eur J Prosthodont Restor Dent,* 2002, 10:27-32; García-Godoy, F et al. Caries progression of white spot lesions sealed with an unfilled resin. *J Clin Pediatr Dent,* 1997, 21:141-143; Robinson, C et al. In vitro studies of the penetration of adhesive resins into artificial caries-like lesions. *Caries Res,* 2001, 35:136-141; Schmidlin, P R et al. Penetration of a bonding agent into de- and remineralized enamel in vitro. *J Adhes Dent,* 2004, 6:111-115). It could be shown that sealants penetrate the body of artificial lesions up to 95% (Gray, G B and Shellis, P. Infiltration of resin into white spot caries-like lesions of enamel: An in vitro study. *Eur J Prosthodont Restor Dent,* 2002, 10:27-32), and reduce the accessible pore volumes within the lesions significantly (Robinson, C et al. In vitro studies of the penetration of adhesive resins into artificial caries-like lesions. *Caries Res,* 2001, 35:136-141). Moreover, it has been observed that sealants are capable to inhibit further lesion progress under demineralizing conditions (Robinson, C et al. Arrest and control of carious lesions: A study based on preliminary experiments with resorcinol-formaldehyde resin. *J Dent Res,* 1976, 55:812-818; García-Godoy, F et al. Caries progression of whit spot lesions sealed with an unfilled resin. *J Clin Pediatr Dent,* 1997, 21:141-143; Robinson et al. In vitro studies of the penetration of adhesive resins into artificial caries-like lesions. *Caries Res,* 2001, 35:136-141).

However, one of the problems in sealing natural enamel lesions is that "pseudo-intact surface layers" have higher mineral contents compared to carious bodies of lesion. As a consequence, these layers inhibit the penetration of the lesion body by the sealing material and may even function as a barrier. In the end, the surface layer may be superficially sealed, but the carious body may be insufficiently penetrated by the resin. At worst, the carious process further proceeds below the "seal".

Efforts have been made to enhance the penetration of an enamel lesion. In an in vitro model, extracted bovine incisors were treated to produce an intact surface layer, a body of lesion and a progressive demineralization front. It has been shown that a 5-second etching of those artificially induced lesions with phosphoric acid resulted in deeper penetration depths (Gray, G B and Shellis, P. Infiltration of resin into white spot caries-like lesions of enamel: An in vitro study. *Eur Prosthodont Restor Dent*, 2002, 10:27-32). Thus, such a pretreatment or "conditioning" of an enamel area by etching could also improve the penetration of sealant in vivo. However, artificially induced enamel lesions differ from natural lesions in that they comprise regular and relatively thin "pseudo-intact surface layers". Natural enamel lesions, in contrast, usually show higher mineralized surface layers of varying thickness. Thus, conditioning with phosphoric acid, although demonstrated as successful in vitro, must not necessarily provide for a benefit in vivo.

Nevertheless, an in vivo study reported that the application of a conventional adhesive onto enamel lesions pre-treated with phosphoric acid gel resulted in retardation of caries progression compared to controls (Ekstrand et al. *Caries Res*, 2004, 38:361). However, patients were monitored for two years only and diagnosis was done by x-raying, a rather insensitive method for analyzing successful penetration. Therefore, the results of this study should be regarded with some caution, as even the authors concede. Moreover, it remains unclear whether this initial success would be seen after longer periods since the rather superficial "seal" might be destroyed due to the physical load in vivo.

Thus, there is still a strong need for an improved non-operative procedure of treating initial enamel lesions in order to inhibit caries progression.

It is therefore an object of the present invention to provide for a method and means enabling improved resin penetration of initial enamel lesions.

SUMMARY OF THE INVENTION

The object of the present invention is solved by a method of infiltrating enamel, comprising the following steps:
 (a) exposing an enamel area to be infiltrated to a conditioner comprising hydrochloric acid;
 (b) exposing the enamel area conditioned in step (a) to an infiltrant;
 (c) curing the infiltrant.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In a further embodiment, the conditioner further comprises additives selected from the group comprising glycerol, highly dispersed silicon dioxide and methylene blue.

In one embodiment, the infiltrant comprises at least one low viscous resin.

In a preferred embodiment, the low viscous resin is selected from the group comprising bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, Bis(acryloxymethyl) triclodecane; BEMA, benzyl methacrylate; SIMA, 3-trimethoxysilane propyl-methacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a particularly preferred embodiment, the low viscous resin is selected from the group comprising polymethacrylic acid and derivatives thereof.

In a most preferred embodiment, the low viscous resin is selected form the group comprising bis-GMA, 2,2-bis[4-(2-hydroxy-3-methacryloxypropoxy)phenyl]propane; UDMA, 1,6-bis(methacryloxy-2-ethoxycarbonylamino)-2,4,4-trimethylhexan; TEGDMA, triethylene glycol dimethacrylate; and HEMA, 2-hydroxyethyl methacrylate.

In a further embodiment, the infiltrant further comprises additives selected from the group comprising CQ, camphoroquinone; BL, benzil; DMBZ, dimethoxybenzoin; CEMA, N-(2-cyanoethyl)N-methylanilin; DMABEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hydroxy-4-methoxy benzophenone; TINP, 2(2'-hydroxy-5'-methylphenyl) benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-methylenebis(6-t-butyl-4-ethylphenol); BPE, benzoic acid phenylester; MMMA, methyl methacrylate methanol adduct; CA, camphoric anhydride; HC ½, 2(3)-endo-hydroxyepicamphor; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

The object of the present invention is further solved by a use of a method of infiltrating enamel according to any of the preceding claims for the prevention and/or treatment of a carious lesion in a subject in need thereof.

In one embodiment, the subject is a mammal, preferably human.

The object of the present invention is also solved by a kit for infiltrating enamel, comprising at least the following:
 (a) a conditioner comprising hydrochloric acid;
 (b) an infiltrant.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In a further embodiment, the conditioner further comprises additives selected from the group comprising glycerol, highly dispersed silicon dioxide and methylene blue.

In one embodiment, the infiltrant comprises at least one low viscous resin.

In a preferred embodiment, the low viscous resin is selected from the group comprising bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate;

BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl) triclodecane; BEMA, benzyl methacrylate; SIMA, 3-trimethoxysilane propyl-methacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a particularly preferred embodiment, the low viscous resin is selected from the group comprising polymethacrylic acid and derivatives thereof.

In a most preferred embodiment, the low viscous resin is selected form the group comprising bis-GMA, 2,2-bis[4-(2-hydroxy-3-methacryloxypropoxy)phenyl]propane; UDMA, 1,6-bis(methacryloxy-2-ethoxycarbonylamino)-2,4,4-trim-ethylhexan; TEGDMA, triethylene glycol dimethacrylate; and HEMA, 2-hydroxyethyl methacrylate.

In a further embodiment, the infiltrant further comprises additives selected from the group comprising CQ, campho-roquinone; BL, benzil; DMBZ, dimethoxybenzoin; CEMA, N-(2-cyanoethyl)N-methylanilin; DMABEE, 4-N,N-diethy-laminobenzoic acid ethyl ester; DMABBEE, 4-N,N-diethy-laminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hy-droxy-4-methoxy benzophenone; TINP, 2(2'-hydroxy-5'-me-thylphenyl) benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-Meth-ylenebis(6-t-butyl-4-ethylphenol); BPE, benzoic acid pheny-lester; MMMA, methyl methacrylate methanol adduct; CA, camphoric anhydride; HC ½, 2(3)-endo-hydroxyepicam-phor; TPP, triphenyl phosphane; TPSb, triphenyl stibane; DMDDA, dimethyl dodecylamine; DMTDA, dimethyl tet-radecylamine; DCHP, dicyclohexyl phthalate; DEHP, bis-(2-ethylhexyl) phthalate; and formaldehyde.

The object of the present invention is also solved by a use of a kit for infiltrating enamel for the prevention and/or treatment of a caries lesion in a subject in need thereof.

In one embodiment, the subject is a mammal, preferably human.

The object of the present invention is also solved by a method for preparing the kit.

The object of the present invention is also solved by the use of hydrochloric acid for the manufacture of a medical product for the prevention and/or treatment of a carious lesion.

In one embodiment, the medical product is based on a gel comprising about 1-30% (w/w) of hydrochloric acid.

In a preferred embodiment, the medical product is based on a gel comprising about 5-15% (w/w) of hydrochloric acid.

In a further embodiment, the medical product further comprises additives selected from the group comprising glycerol, highly dispersed silicon dioxide and methylene blue.

The object of the present invention is also solved by a method for manufacturing the medical product.

The object of the present invention is also solved by an infiltrant comprising at least one low viscous resin.

In one embodiment, the low viscous resin is selected from the group comprising bis-GMA, 2,2-bis[4-(2-hydroxy-3-methacryloxypropoxy)phenyl]propane; bis-PMA, propoxy-lated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycar-bonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacry-late; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl) triclodecane; BEMA, benzyl methacrylate; SIMA, 3-trimethoxysilane propyl-methacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a preferred embodiment, the low viscous resin is selected from the group comprising polymethacrylic acid and derivatives thereof.

In a particularly preferred embodiment, the low viscous resin is selected form the group comprising bis-GMA, 2,2-bis[4-(2-hydroxy-3-methacryloxypropoxy)phenyl]propane; UDMA, 1,6-bis(methacryloxy-2-ethoxycarbonylamino)-2, 4,4-trimethylhexan; TEGDMA, triethylene glycol dimethacrylate; and HEMA, 2-hydroxyethyl methacrylate.

In a further embodiment, the infiltrant further comprises additives selected from the group comprising CQ, campho-roquinone; BL, benzil; DMBZ, dimethoxybenzoin; CEMA, N-(2-cyanoethyl)N-methylanilin; DMABEE, 4-N,N-diethy-laminobenzoic acid ethyl ester; DMABBEE, 4-N,N-diethy-laminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hy-droxy-4-methoxy benzophenone; TINP, 2(2'-hydroxy-5'-me-thylphenyl) benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-Meth-ylenebis(6-t-butyl-4-ethylphenol); BPE, benzoic acid pheny-lester; MMMA, methyl methacrylate methanol adduct; CA, camphoric anhydride; HC ½, 2(3)-endo-hydroxyepicam-phor; TPP, triphenyl phosphane; TPSb, triphenyl stibane; DMDDA, dimethyl dodecylamine; DMTDA, dimethyl tet-radecylamine; DCHP, dicyclohexyl phthalate; DEHP, bis-(2-ethylhexyl) phthalate; and formaldehyde.

The object of the present invention is further solved by a method for preparing an infiltrant.

The term "exposing" as used herein refers to any procedure by which the enamel is provided with the conditioner or the infiltrant. Mostly, an exposure will be achieved by simple application, e.g. by spreading. For that purpose, the kit may additionally comprise one or more devices suitable for supporting the application, e.g. a brush, a sponge, a tissue, a pipette, a syringe or such.

It is considered by the present invention that the conditioner may be removed prior to application of the infiltrant. Thus, the kit may additionally comprise any device for that purpose.

It is further considered by the present invention that surplus infiltrant may be removed. Thus, the kit may additionally comprise any device for that purpose.

Preferably, the conditioner is allowed to remain applied for about 90-120 seconds, more preferably, the conditioner is allowed to remain applied for about 120 seconds.

Preferably, the infiltrant is allowed to remain applied for up to about 120 seconds, more preferably, the infiltrant is allowed to remain applied for about 120 seconds.

Preferably, the infiltrant is applied twice.

An "enamel area to be infiltrated" preferably is an area comprising a carious lesion. However, in order to prevent such lesions, i.e. for prophylaxis, any carious damage may be also absent in this area.

The conditioner may alternatively be based on an aqueous solution or may also be embedded in a plaster.

It is also considered by the present invention that the conditioner may additionally comprise phosphoric acid up to about 40% (w/w), preferably in the range of about 20% to 37% (w/w).

"Curing of the infiltrant" is preferably achieved by light-induced polymerization.

To enable access to the approximal surface, a separation of the carious teeth could be performed using orthodontic elastics. This technique is well documented for diagnostic purposes.

The resins according to the present invention are further considered for use as dental adhesives and/or fissure sealants.

Said resins cited above may be used, e.g. within the infiltrant of the present invention, either separately or in any combination thereof.

In conclusion, the present invention provides for an improved penetration of initial enamel lesions by an infiltrant. Within the prior art, methods of sealing enamel are available which, however, bear the risk of only superficially sealing the "pseudo-intact surface layer" but leaving the body of lesion insufficiently penetrated by the resin. Using the method and means, e.g. the conditioner and/or the low viscous resins, according to the present invention, occlusion of the body of lesion becomes possible.

First, by exposing an enamel area to be infiltrated to the conditioner comprising hydrochloric acid, the "pseudo-intact surface layer" is removed such that infiltration of carious areas by the infiltrant is greatly facilitated. Second, the resins cited above exhibit very low viscosity properties, and thus the infiltrant readily reaches the pores of the lesion to occlude them.

By using the method and means according to the present invention, invasive treatment of an enamel lesion may be prevented or at least delayed. Due to the non-operative character of the sealing procedure, the patient's compliance will be greatly enhanced. The method is well practicable with low costs. Finally, the inventive method may represent a therapeutic link between pure prophylaxis and invasive treatment of caries.

As used in this specification and the appended claims, the singular forms "a", "an", and "the" include plural reference unless the context clearly dictates otherwise.

DETAILED DESCRIPTION OF THE INVENTION

In the following, the invention should be further illustrated by making reference to FIGS. 1-3 and to Examples 1 and 2.

Figure 1:
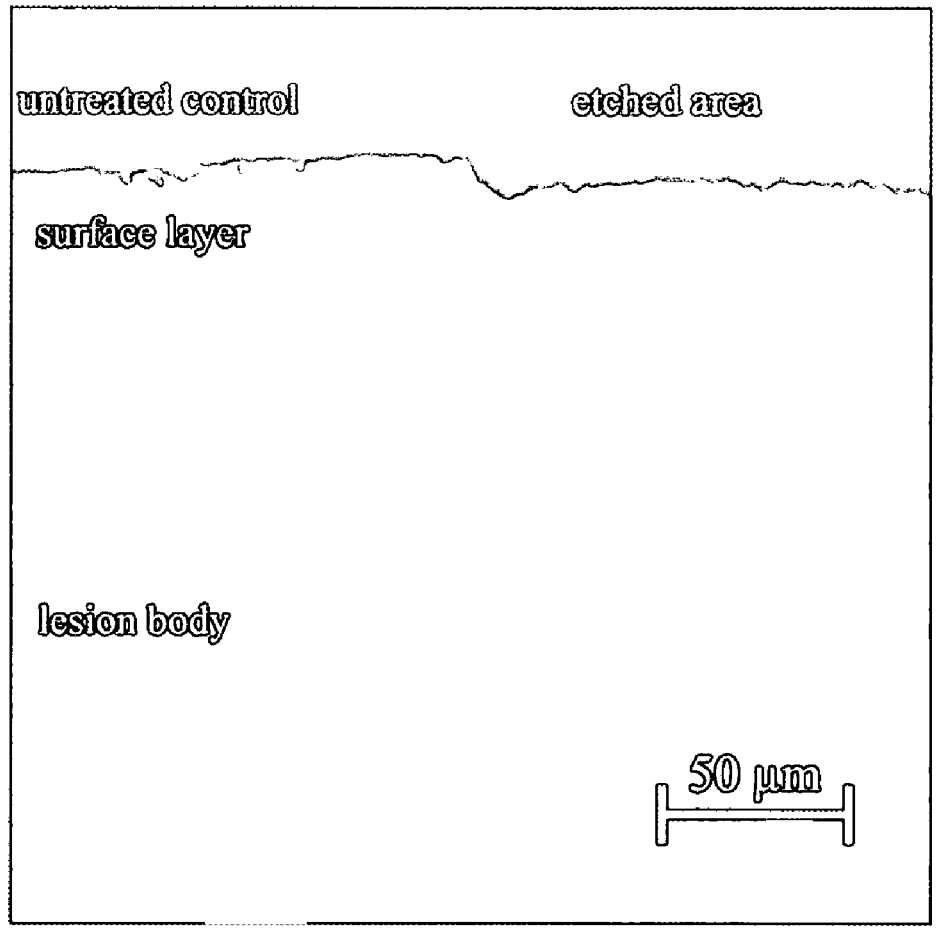
FIG. 1 shows an initial enamel carious lesion after conditioning with 37% phosphoric acid gel for 30 seconds.
Figure 2:
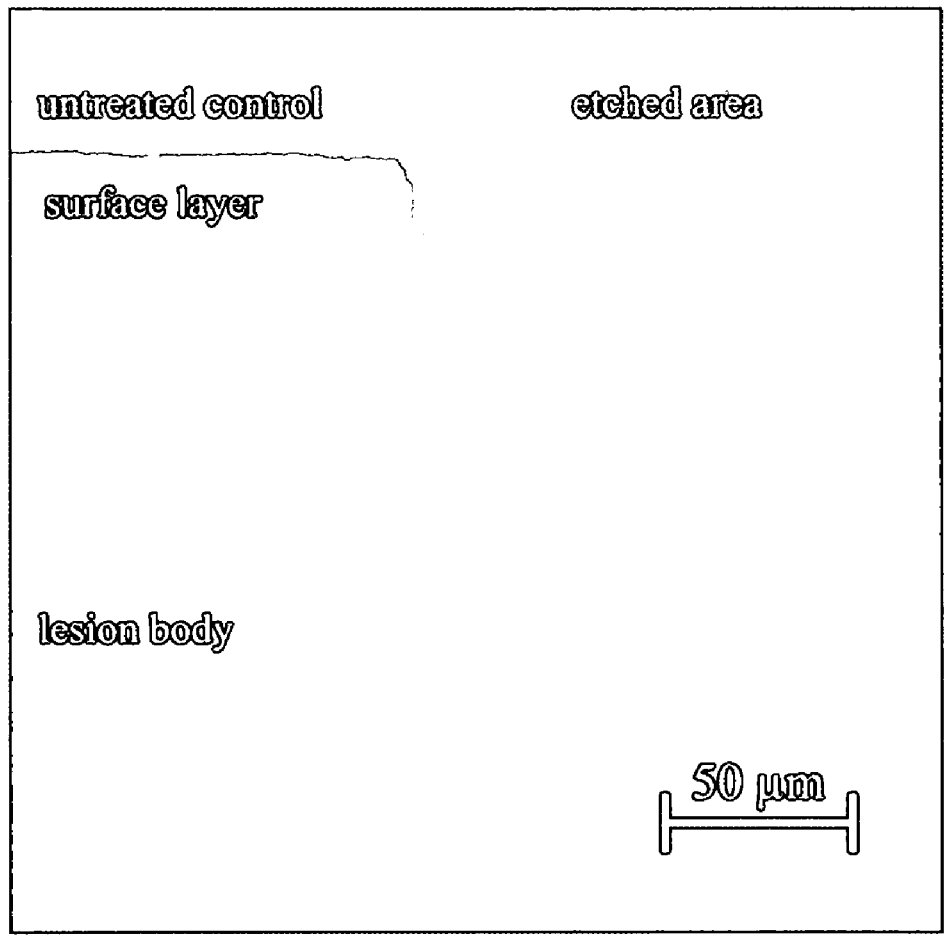
FIG. 2 shows an initial enamel carious lesion after conditioning with 15% hydrochloric acid gel for 120 seconds.
Figure 3:
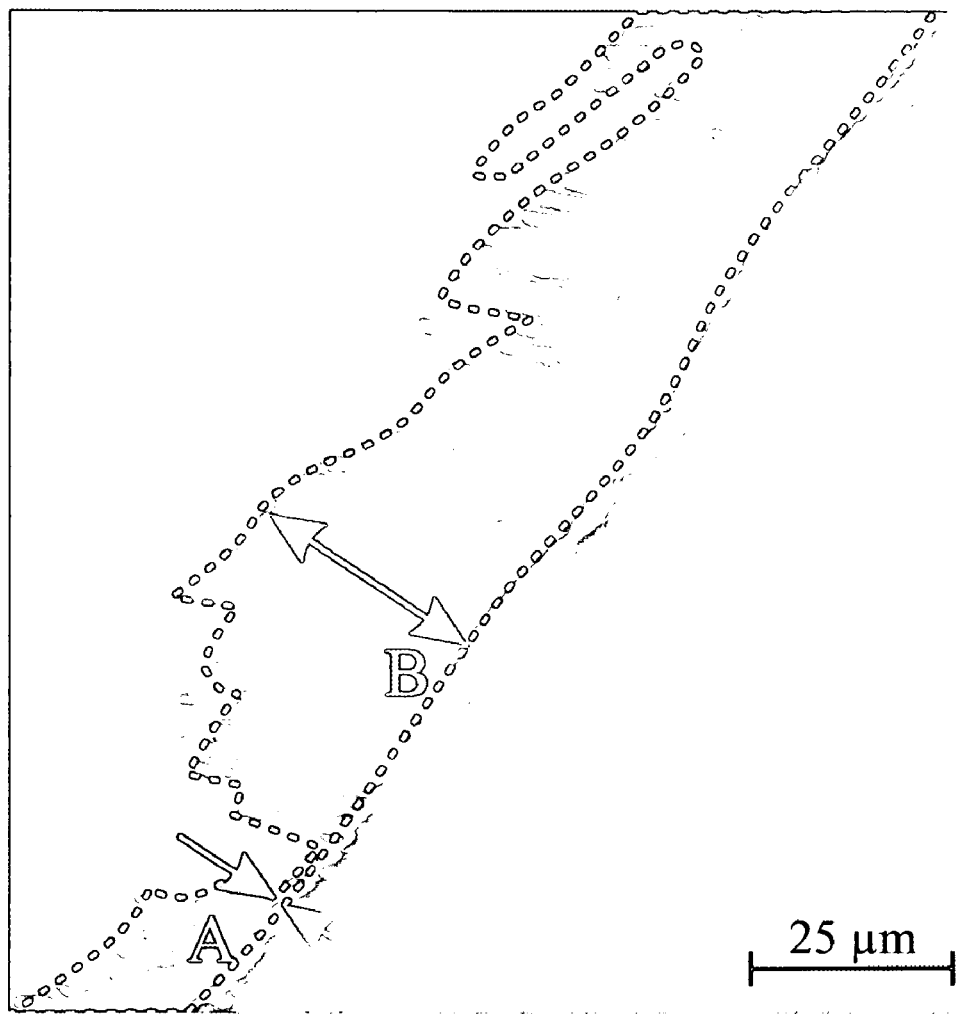
FIG. 3 shows a partially infiltrated initial enamel carious lesion.

FIGS. 1-3 show results obtained by the Confocal Laser Scanning Microscope (CLSM) imaging technique.

FIG. 1 shows an initial enamel carious lesion after conditioning with 37% of phosphoric acid gel for 30 seconds.

FIG. 2 shows an initial enamel carious lesion after conditioning with 15% hydrochloric acid gel for 120 seconds.

FIG. 3 shows a partially infiltrated initial enamel carious lesion.

EXAMPLES

Example 1

Effect of the Pre-treatment with a Conditioner Comprising Hydrochloric Acid

1. Material and Methods 1.1 Sample Preparation

Extracted human molars and premolars, showing approximal white spots were cut across the demineralizations. One-hundred-twenty lesions confined to the outer enamel were selected. The cut surface as well as half of each lesion, thus serving as control, was covered with nail varnish. Subsequently, the lesions were etched with either phosphoric (37%) or hydrochloric (5% or 15%) acid gel for 30 to 120 seconds (n=10).

1.2 Visualization

The specimens were dried for 5 minutes in a silicone hose, closed at one end with a stopper, and separated with silicone rings. Subsequently, Spurr's resin (Spurr, A R. A low-viscosity epoxy resin embedding medium for electron microscopy. *J Ultrastruct Res*, 1969, 26:31-43), labeled with 0.1 mmol/l of the fluorescent dye Rhodamine B Isothiocyanate (RITC), was doused over the specimens and the hose was closed with another stopper. The resin was cured in an autoclave (Ivomat IP3; Ivoclar Vivadent, Schaan, Liechtenstein) at 0.8 MPa and 70° C. for 8 hours. Under this pressure, the very low viscous resin penetrated into the remaining pores of the lesion. After curing, the specimens were cut, fixed on object holders, parallelized and polished up to 4000 grit (Exakt Mikroschleifsystem; ExaktApparatebau). This infiltration technique was termed VIsualisation by Resin INfiltration (VIRIN).

1.3 CLSM Imaging

The specimens were studied using a Confocal Laser Scanning Microscope (CLSM) (Leica TCS NT; Leica, Heidelberg, Germany). The excitation light was generated with an Ar/Kr-Laser and had a maximum wavelength at 560 nm. The images were recorded in fluorescent mode. The emitted light was conducted through a 590 nm long pass filter to make sure that only fluorescent light was detected and reflected light was suppressed. Specimens were observed with a 40× objective using oil immersion. The observed layer was approximately 10 μm below the surface. Laser beam intensity and photo multiplier amplification were kept constant during the investigation. The images (250×250 μm) were taken with a resolution of 1024×1024 pixels and 256 pseudo color steps (red/black) and analyzed using the ImageJ Program (NIH; Rockville Pike, Md., USA).

2. Results

The thickness of the surface layers in the control and the etched parts as well as the erosions in the sound and diseased tissues were measured. Etching with $H_3PO_4$ gel for 30 seconds did not alter the thickness of the surface layer significantly ($p>0.05$; t-test). However, the surface layer reduction was significantly increased in lesions etched with 15% HCl gel for 90 seconds compared to those etched with $H_3PO_4$ gel for 30 seconds or 90 seconds (p<0.05; ANOVA). No significant differences in the depths of erosion in the lesions compared to sound enamel could be observed (p>0.05; t-test).

In FIG. 1, it is shown that pre-treatment of initial enamel carious lesions with 37% of phosphoric acid gel for 30 seconds resulted in only insufficient etching of the "pseudo-intact surface layer". Thus, this kind of pre-treatment is not capable of destabilizing the surface layer to an extent necessary for optimal penetration of the infiltrant. In consequence, sealing will be only superficial. Incomplete infiltration, however, does not protect from organic acids and dissolution of enamel and erosion will further proceed. In FIG. 2, it is shown that pre-treatment with 15% of hydrochloric acid gel for 120 seconds resulted in complete removal of the "pseudo-intact surface layer".

It can be concluded that a reliable reduction of the surface layer can be achieved by etching with 15% hydrochloric acid gel for 90-120 seconds.

Example 2

Penetration of Infiltrant in the Presence or Absence of a "Pseudo-Intact Surface Layer"

1. Material and Methods

Natural enamel lesions were etched with 15% hydrochloric acid for 30 seconds. Several experimental infiltrants and the commercial adhesive Excite (Vivadent, Schaan, Lichtenstein), respectively, each labeled with the fluorescent dye RITC, were applied on the lesions using a micro brush. After a penetration time of 120 seconds the overlying material was wiped away using a cotton roll and the resins were light cured for 15 seconds (Translux CL; Heraeus Kulzer). The preparation for the CLSM observation was carried out as described above, except that the embedding resin was labeled with the fluorescent dye Fluoresceine Isothiocyanate (FITC). The CLSM observation was carried out as described above except that the double fluorescence mode was used for RITC/FITC observation.

2. Results

In FIG. 3, it is shown that enamel areas covered by a "pseudo-intact surface layer" (A, dark surface zone) are not penetrated by the infiltrant (arrows). In contrast, in the absence of this layer (B) the infiltrant readily has penetrated the area below (double-arrow).

Thus, in areas where the "pseudo-intact surface layer" was removed by the etching gel, an infiltration of the lesion could be achieved. In areas where the "pseudo intact surface layer was not completely removed by the conditioning agent no significant infiltration of the lesion was observed.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of infiltrating enamel, comprising the following steps:
   (a) removing a portion of enamel area to be infiltrated by exposing said enamel to a conditioner comprising about 5-30% (w/w) hydrochloric acid for at least 30 seconds;
   (b) exposing the enamel area conditioned in step (a) to an infiltrant; and
   (c) curing the infiltrant.

2. The method according to claim 1, wherein the conditioner comprises a gel comprising about 5-30% (w/w) of hydrochloric acid.

3. The method according to claim 1, wherein the conditioner comprises a gel comprising about 5-15% (w/w) of hydrochloric acid.

4. The method according to claim 1, wherein the conditioner further comprises an additive selected from the group consisting of glycerol, highly dispersed silicon dioxide, and methylene blue.

5. The method according to claim 1, wherein the infiltrant comprises at least one low viscous resin.

6. The method according to claim 5, wherein the low viscous resin is selected from the group consisting of bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-entanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl) triclodecane; BEMA, benzyl methacrylate; SIMA, 3-trimethoxysilane propylmethacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

7. The method according to claim 5, wherein the low viscous resin comprises polymethacrylic acid or a derivative thereof.

8. The method according to claim 7, wherein the low viscous resin is selected from the group consisting of bis-GMA, 2,2-bis[4-(2-hydroxy-3-methacryloxypropoxy)phenyl]propane; UDMA, 1,6-bis(methacryloxy-2-ethoxycarbonylamino)-2,4,4-trimethylhexan; TEGDMA, triethylene glycol dimethacrylate; and HEMA, 2-hydroxyethyl methacrylate.

9. The method according to claim 5, wherein the infiltrant fruther comprises an additive selected from the group consisting of CQ, camphoroquinone; BL, benzil; DMBZ, dimethoxybenzoin; CEMA, N-(2-cyanoethyl)N-methylanilin; DMABEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylliexyl ester; DMAEMA, N,N-diethyl aminoethyl methacrylate; DEMAEEA, N,N-(bis-ethylmetacrylate)-2-ethoxyethylamine; HMBP, 2-hydroxy-4-methoxy benzophenone; TINP, 2(2'-hydroxy-5'-methylphenyl)benzotriazol; TIN326, Tinuvin 326; TIN3SO, Tinuvin 350; Tin328, Tinuvin 328; HQME, hydroxyquinone monomethyl ester; BHT 2,6-di-t-butyl-4-methyl phenol, MBP 2,2-methylene-bis(6-t-butylphenol); MBEP, 2,2-methylenebis(6-t-butyl-4-ethylphenol); BPE, benzoic acid phenylester; MMMA, methyl methacrylate methanol adduct; CA, camphoric anhydride;

HC ½, 2(3)-endo-hydroxyepicamplior; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

10. A method of infiltrating enamel for the prevention and/or treatment of a carious lesion in a subject in need thereof comprising the following steps:
   (a) removing a portion of enamel area to be infiltrated by exposing said enamel to a conditioner comprising about 5-30% (w/w) hydrochloric acid for at least 30 seconds;
   (b) exposing the enamel area conditioned in step (a) to an infiltrant; and
   (c) curing the infiltrant.

11. The method according to claim 10, wherein the subject is a human.

12. A method for infiltrating enamel for the prevention and/or treatment of a carious lesion in a subject in need thereof, using a kit, said method comprising the following steps:
   (a) removing a portion of enamel area to be infiltrated by exposing said enamel to a conditioner comprising about 5-30% (w/w) hydrochloric acid for at least 30 seconds;
   (b) exposing the enamel area conditioned in step (a) to an infiltrant; and
   (c) curing the inifiltrant;
wherein the kit comprises the conditioner and the infiltrant.

13. The method according to claim 12, wherein the subject is a human.

* * * * *

UNITED STATES PATENT AND TRADEMARK OFFICE
CERTIFICATE OF CORRECTION

PATENT NO. : 7,485,673 B2
APPLICATION NO. : 11/040442
DATED : February 3, 2009
INVENTOR(S) : Hendrik Meyer-Luckel, Sebastian Paris and Andrij M. Kielbassa It is certified that error appears in the above-identified patent and that said Letters Patent is hereby corrected as shown below:

On the Title Page Item (73) the name of the Assignee reads "Charite-Universitatsmedizin Berline, Berlin (DE)"

The correct name of the Assignee should read "Charite-Universitatsmedizin Berlin, Berlin (DE)"

Signed and Sealed this

Eleventh Day of August, 2009

David J. Kappos
*Director of the United States Patent and Trademark Office*